(12) United States Patent
Rosero (10) Patent No.: US 8,024,020 B2
(45) Date of Patent: Sep. 20, 2011

(54) SYSTEM AND METHOD FOR STIMULATION OF BIOLOGIC SIGNALS IN A BIO-ELECTRO-PHYSIOLOGIC MATRIX

(75) Inventor: Spencer Rosero, Pittsford, NY (US)

(73) Assignee: University of Rochester, Rochester, NY (US)

( * ) Notice: Subject to any disclaimer, the term of this patent is extended or adjusted under 35 U.S.C. 154(b) by 1537 days.

(21) Appl. No.: 11/397,627

(22) Filed: Apr. 5, 2006

(65) Prior Publication Data

US 2006/0252976 A1 Nov. 9, 2006

Related U.S. Application Data

(63) Continuation-in-part of application No. PCT/US2005/15380, filed on May 4, 2005.

(51) Int. Cl.
*A61B 5/1455* (2006.01)

(52) U.S. Cl. ........................................ 600/310; 600/341

(58) Field of Classification Search ........... 600/309–344
See application file for complete search history.

(56) References Cited

U.S. PATENT DOCUMENTS

| | | | |
|---|---|---|---|
| 5,674,251 A | 10/1997 | Combs et al. | |
| 5,814,089 A | 9/1998 | Stokes et al. | |
| 5,846,188 A * | 12/1998 | Palti | 600/300 |
| 5,987,352 A | 11/1999 | Klein et al. | |
| 6,011,984 A * | 1/2000 | Van Antwerp et al. | 600/317 |
| 6,141,588 A | 10/2000 | Cox et al. | |
| 6,412,490 B1 | 7/2002 | Lee | |
| 6,544,193 B2 * | 4/2003 | Abreu | 600/558 |

* cited by examiner

*Primary Examiner* — Eric Winakur
*Assistant Examiner* — Marjan Fardanesh
(74) *Attorney, Agent, or Firm* — Blank Rome LLP (57) ABSTRACT

An implantable device for monitoring physiological changes in an organism is disclosed. The device includes a matrix positioned proximate a biological material of the organism, an irradiation device associated with the matrix for exposing the biological material to radiation, and a sensor device associated with the matrix for detecting a response of the biological material to the irradiation. The response can be used to remotely detect a characteristic of the biological material.

21 Claims, 6 Drawing Sheets

SYSTEM AND METHOD FOR STIMULATION OF BIOLOGIC SIGNALS IN A BIO-ELECTRO-PHYSIOLOGIC MATRIX

CROSS-REFERENCE TO RELATED APPLICATIONS

The present application is a continuation-in-part of related International Application No. PCT/US2005/015380 filed May 4, 2005.

BACKGROUND OF THE INVENTION

1. Field of Invention

The present invention is generally related to implantable sensors and, more particularly, to a device for facilitating two way communication and stimulation between biologic material and electronic devices.

2. Description of Prior Art

The role of implantable medical devices to monitor and treat disorders of the heart, brain, nervous system and musculoskeletal system is increasingly becoming a major part of therapy and has been facilitated by recent advances in technology. Diseases that disrupt the heart, brain, or nervous system's ability to communicate or function normally include heart rhythm disorders such as ventricular fibrillation, which could be life threatening, heart block, and neurologic disorders such as epilepsy, multiple sclerosis, spinal injury, and dysautonomias. Diseases that affect the secretion and regulation of biochemical signals include diabetes and cancer. Pharmacologic therapy is currently used to treat these disorders and may be integrated with implantable and non-implantable drug delivery systems as well as the use of pacemakers and defibrillators to treat heart rhythm disorders are available.

The treatment of brain and nervous system disorders includes deep brain stimulation methods involve placing wires within the brain and attaching them to an implantable device to stimulate the target areas of the nervous system in order to control epilepsy, hypertension, as well as movement disorders such as Parkinson's disease. Surgical procedures have been proposed for these disorders. For example, open brain surgery for the placement of leads (wires) that are positioned through brain tissue to reach the target sites then tunneled under the skin to a device implanted elsewhere, placing wires in the heart to provide a defibrillation shock (established procedure) using the blood vessels as the conduit to reach the heart.

The treatment of epilepsy has traditionally been limited to medications or aggressive brain surgery to remove affected areas responsible for the seizures. In many ways, epilepsy has characteristics that are shared with the heart during ventricular fibrillation. Both disorders are associated with an abrupt disturbance of a regular (normal) electrical rhythm resulting in chaotic electrical activation of the heart or brain which causes a seizure or sudden cardiac death. A common thread among these technologies is their limitation to lead (wire) based technologies that rely on mechanical or electrical sensors to determine the status of the target organ and do not specifically record non-electrical cellular activity However, current technologies, such as those shown in U.S. Pat. Nos. 6,412,490 and 5,987,352, are hampered by the use of non-biological sensing elements such as electrodes or imaging based sensing. Complex steps and risks are involved in obtaining venous vascular access and placement of the transvenous lead in the patient population requiring the defibrillation. In addition, when neurologic treatment requires an implantable lead, the same problems associated with lead infection, extraction when infected, as well as the mode of reaching the target organ with the least amount of trauma is an important consideration.

SUMMARY AND OBJECTS OF THE INVENTION

Accordingly, it is an object of the present invention to provide an implantable device for monitoring physiological changes in an organism such that the device can be operated without leads.

It is another object of the invention to provide an electronic device embedded with cells of an organism that is used to detect and/or monitor substances and physiologic responses associated with those cells.

It is another object of the invention to monitor, using a photodetector and/or camera, the photonic, fluorescence, and optical characteristics of cells that are positioned within a support matrix.

It is still another object of the invention to provide a matrix positioned near a biological material that supports a stimulation device and a detector device that detects a response of the biological material to stimulation, primarily in the form of visible, infrared, and ultraviolet electromagnetic radiation.

It is another object of the invention to provide a device that operates in conjunction with cells obtained from a living organism, and, therefore, is capable of allowing heat and mass transfer to exchange from the biological material inside the matrix and does not interfere with normal or modified cellular physiology.

It is still another object of the invention to provide a device that is self sustaining inside a living organism and that communicates information by way of a wireless communication device, such as by using an ultrasonic communication devices and between a communications transmitter and a computer-implemented controller.

It is another object of the invention to provide a device that is capable of monitoring or detecting both chemical and physical changes in the biological material.

Briefly described, those and other objects and features of the present invention are accomplished, as embodied and fully described herein, by an implantable device that is composed of an electronic component and a biologic materials component. The purpose is for the electronic component to communicate (i.e., sensing and stimulation) with the biologic material it contacts. The biologic component consists of the cells of interest (cardiac/vascular/etc.) which are biopsied/obtained from the patient and grown in a complex collagen or other biocompatible support matrix. The cells may be genetically engineered for specific function as well as be derived from a source other than the patient. The matrix is lined with micron sized sensing electrodes that perform various types of sensing such as accelerometer, pressure, flow, temperature, strain/shear stress and electrical discharge/signals.

The matrix is integrated (various shapes/sizes-individualized) to the primary circuit board that translates the signals received to a predetermined format for processing and/or relaying to another module. As many individual matrix devices as needed for a specific function can be linked in a network. Communication between devices can be accomplished via radio frequency, fiber optic, analog electrical subcutaneous signaling, using blood as communication medium or direct metallic conducting media (i.e., wires), or a combination of the above.

The specificity and sensitivity of implanted and external devices is improved by using biologic tissue itself as the signal specific sensor that is integrated into the device. The biologic cells are complex and can manage multiple inputs and outputs. In addition, the cells allow for miniaturization of the sensing device when integrated to an electronic circuit that then translates the individual cell responses to a digital signal. The cells assigned to perform the "sensor" function are integrated directly to the electronic component or within the vicinity to allow detection of the cellular matrix response.

The aforementioned objects and features of the present invention are also accomplished, as embodied and fully described herein, by a method for monitoring physiological changes in an organism using the implantable device described above.

With those and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

In describing a preferred embodiment of the invention illustrated in the drawings, certain specific terminology will be used for the sake of clarity. However, the invention is not intended to be limited to that specific terminology, and it is to be understood that the terminology includes all technical equivalents that operate in a similar manner to accomplish the same or similar result.

Figure 1:
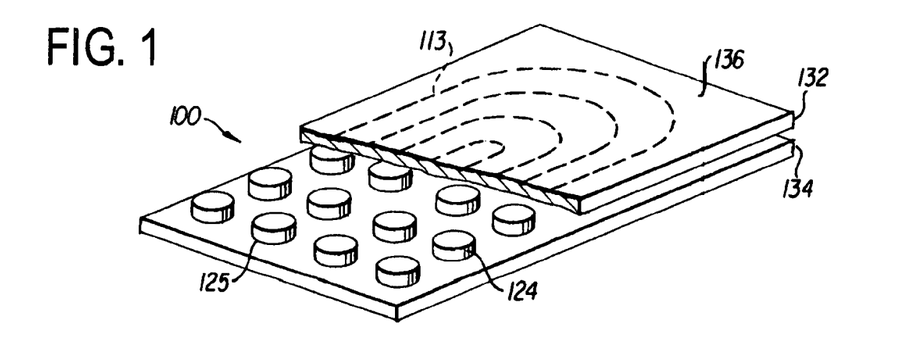
FIG. 1 is a perspective drawing of a biologic interface using a cell based platform matrix.
Figure 2:
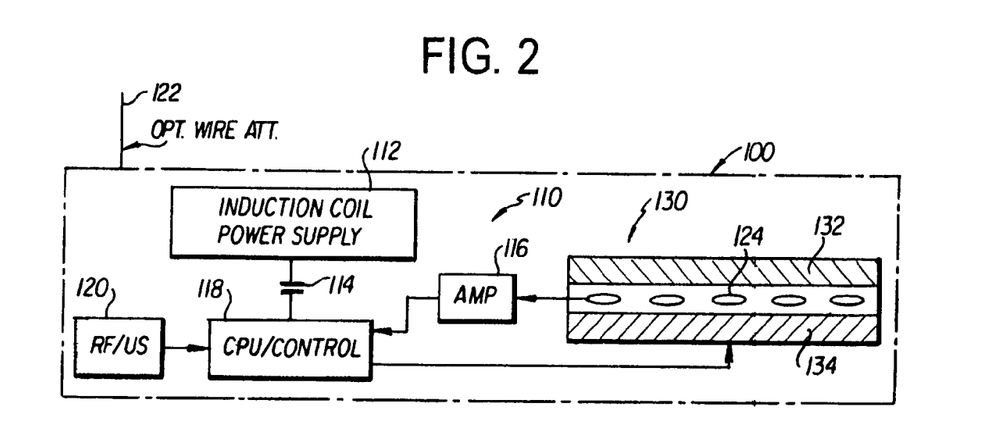
FIG. 2 is a diagram showing the electronic components and the biologic interface.

Referring to the drawings, FIGS. 1 and 2 show the bio-electro-physiologic device 100 of the present invention. The device 100 includes an electronics portion 110 and a biologic materials portion or matrix interface 130. The electronics 110 include a power supply 112, amplifier 116, controller 118, communication device 120 and optional wire connector 122, and electrodes or electrode array 124. The biologic interface 130 includes two layers of cells 132, 134.

However, the interface 130 can have any number of layers with various geometries, including one layer or multiple cell layers.

The cell layers 132, 134 are layered along the electrode array 124 and placed within three-dimensional (i.e., multi-layered) matrices and not limited to such a layer on a two-dimensional plate. The electrodes 124 may also be arranged in a three dimensional configuration, and need not be a single layer array. The electrode array 124 and cell layers 132, 134 are placed so that the cell layers 132, 134 have a thickness of generally no more than about 0.5-1 mm so that the cells receive ample nutrients including oxygen exposure. The electrodes 124 are formatted as an array that forms a layer which is sandwiched between the two cell layers 132, 134.

The electrodes 124 can be positioned anywhere within the cell layers 132, 134 based on the particular application. For instance, if a single cell layer (several cells thick) is used for the biologic interface 130, the electrodes 124 can be sandwiched in the middle or positioned at the surface of that cell layer. In addition, the other electronic components of the electronics portion 110 can optionally be located within the biologic interface 130. Other electrical or non-electrical sensors 125 can also be positioned within the biologic interface 130, either together with the electrodes 124 or instead of the electrodes 124, depending on the anatomy of the site and the desired application. For instance, sensors 125 can measure pressure, flow, pH, oxygen saturation, shear forces, electrical sensing of voltage, capacitance, current, and photodetection of electromagnetic radiation, as well as stretch or pressure changes. According, for example, to measure blood flow or blood related substances, the sensor 125 is placed at the surface of the interface 130 so that it is exposed to the patient's blood.

In accordance with a preferred embodiment of the invention, the power supply 112 is an induction coil 113 that is positioned on the top of the device 100 so that the device 100 is independently powered. The induction coil 113 is preferably woven into the architecture of the device 110 so as to minimize its size. However, the coil 113 can be located in any suitable location, such as inside the biologic interface 130. The capacitor 114 holds energy in storage to power the device and minimize battery use. In addition, the capacitor 114 allows for the storage and delivery of a stimulus when needed, such as a high voltage stimulus. Any level of stimulation can be provided depending on the application. The power supply 112 and/or capacitor 113 can provide cardiac defibrillation up to about 2,000 volts, or only power the electronic components for sensing. The power supply 112 may be a discrete battery source.

Figure 6:
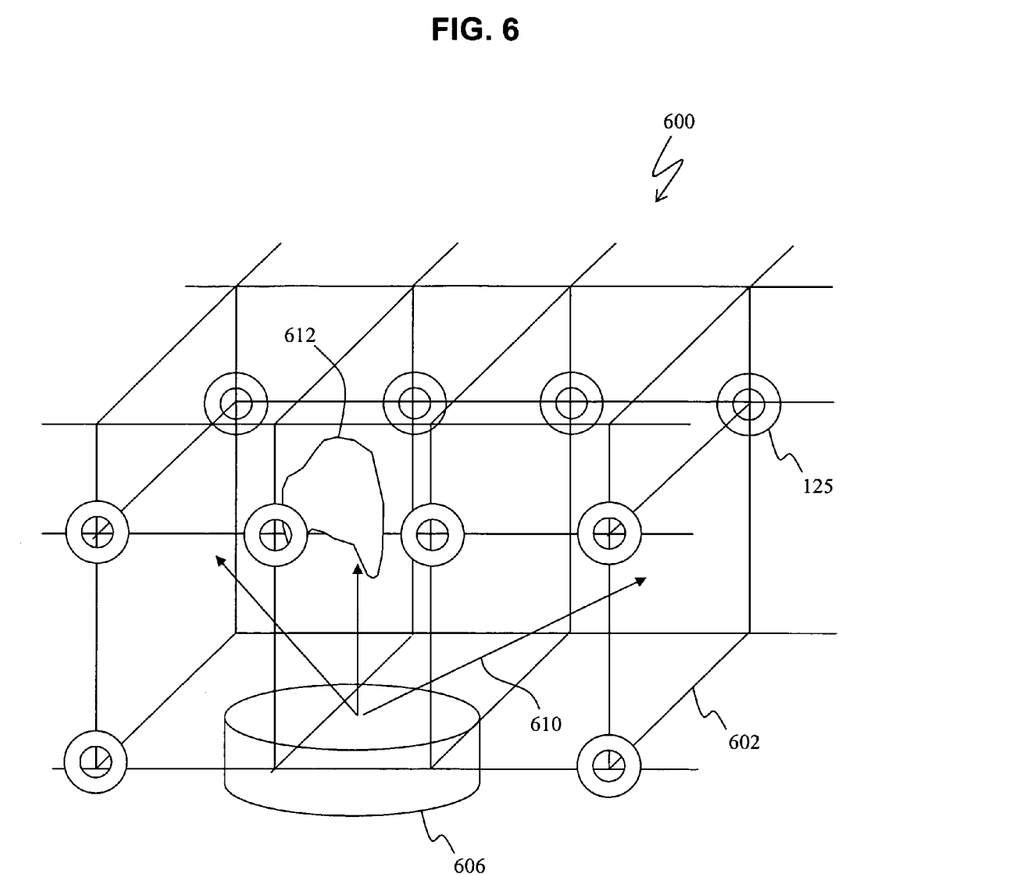
FIG. 6 is a drawing of an embodiment of the invention in the form of a complex collagen or other biocompatible support matrix supporting a plurality of sensors.

The electrodes 124 and/or sensors 125 can be mounted on a flat surface for a two-dimensional basic device, as shown in FIG. 1. Or, as shown in FIG. 6 the electrodes 124 and/or sensors 125 can be mounted in a three-dimensional device with a lattice framework in which the electrodes 124 and/or sensors 125 are positioned anywhere and the cells grown in the lattice framework to maximize surface area contact and allow for nutrient/metabolic products to traverse the matrix. The term lattice is not intended to limit the matrix to a set of evenly spaced-apart support member, but could instead be a more amorphous structure resembling, for example, a sponge-like structure having walls and cavities of different shapes and sized. The electrodes 124 and/or sensors 125 are built into the matrix architecture, so that the electrodes 124 and/or sensor 125 are integrated with the matrix interface 130. The electrodes 124 and/or sensors 125 are connected to the controller 118 and amplifier 116 by micro-welding or by wiring that extends back to the controller 118 and amplifier 116.

The controller 118 can be a processor or the like which is utilized to control operation of the device 100. The output of the controller 118 is connected to the electrodes 124 and sensors 125, and the outputs of the electrodes 124 (which can also serve as an electrical sensor) and sensors 125 are connected to the amplifier 116. The communication device 120 can be a radio frequency (RF) and/or ultrasonic transceiver, or a hard-wired transceiver that makes use of the wire connector 122. Both RF and ultrasonic communications can be used either alone or in combination to reduce information noise for a particular application. If the device is in an electrically noisy environment, then ultrasonic communication may be more suitable.

The electronics 110 are preferably solid state microcircuitry such as MicroElectroMechanical System (MEMS) components. For instance, the electrodes 124 and/or sensors 125 are preferably in the range of several microns or several millimeters. However, any suitable size can be used depending on the application and the cells of interest as well as the signal to be detected.

The controller 118 sends various signals to the electrodes 124 to control both the sensing performed by the sensors 125 and the stimulation performed by the electrodes 124. For instance, the controller 118 sends a sense control signal that signals the sensors 125 to perform various types of sensing. The controller 118 can also send a stimulation signal that causes the electrodes 124 to generate a stimulus output of certain voltage. The stimulus output can have a single pulse or have multiphasic waveforms that vary in frequency. The stimulation signal causes the electrodes 124 to either stimulate the target organ or stimulate or modulate the cells within the matrix interface 130.

The sensors 125 receive the signal from the controller 118 and sense patient conditions or conditions of the cell layers 132, 134. The sensors 125 output the sensed conditions in the form of an electrical signal or the cells deformation of a micro-mechanical device that senses pressure from the attached cells 132, 134. The sensors 125 transmit the sensed signal back to the controller 118 via the amplifier 116. The amplifier 116 removes ambient electrical noise and allows the detection of the physiologic signal of interest. An analog to digital (A/D) converter can also be connected between the amplifier 116 and the controller 118 to convert the signal into a format that is suitable for use by the controller 118. The controller 118 analyzes the signals received from the sensors 125 to determine the conditions sensed by the sensors 125. Based on those sensed conditions, the controller 118 may then generate a stimulation signal that is sent to the electrodes 124 to impart a stimulation to the patient or cell layers 132, 134. A storage device, such as memory, may also be provided to retain data.

The controller 118 translates the signals received to a predetermined format suitable for evaluation. The controller 118 can either analyze the signal itself or forward the signal to another module (such as an infusion pump) for processing. As many individual matrix devices as needed for a specific function can be implanted in a patient and linked together to form a network. Communication between the devices is accomplished by the communications device 120 via radio frequency, fiber optic, analog electrical subcutaneous signaling using blood (which is a conductor) as the communication medium or direct metallic conducting media (i.e., wires) or a combination of the above. In addition, the communications device 120 permits the device 100 to exchange information with a computer located external to the patient. Accordingly, information can be sent from the device 100 to a computer for analysis and review by a physician. And, information can be sent from the computer to the device 100 to modify operation of the controller 118.

Though any number of electrodes 124 can be used, there are preferably at least two electrodes 124. The sensors 125 provide a high resolution output depending on the application (for example about 1,000 Hz for cardiac signals). The sensors 125 can perform any suitable types of sensing such as accelerometer, shear stress, pressure, flow, temperature, chemical conditions and electrical discharge/signals. The accelerometer, for instance, provides data about the movement of a target organ or a person or a position of the person as well as activity of the person as a whole or the target organ. Moving substances such as blood or fluid can also be measured. Conformational cell changes (i.e., the shape changes due to contraction or expansion) are detected by changes in pressure or shear stress in the biologic portion 130.

The biologic materials portion 130 provides an interface between the electronic components 110 to communicate (i.e., sensing and stimulation) with the biologic material it contacts. The cell layers 132, 134 integrate the device 100 with the patient's body. Further to the preferred embodiment, the cell layers 132, 134 form a matrix of intercellular tissue.

The cell layers 132, 134 are cells of interest (such as cardiac, vascular, bone, tissue, or cartilage, depending on the application) which are biopsied or otherwise obtained from the patient and grown in a complex collagen matrix. The collagen matrix, or other biocompatible support matrix is integrated with a support (such as a sponge) that can be either a metallic or inert and nonconductive framework that supports the cells and electrodes as best shown in FIG. 6. Since the cells are cells of interest from the patient, they are able to survive once implanted. The collagen matrix is a biocompatible substance that allows the healthy growth and adhesion of cells. Collagen is preferred, but any substance can be used that has biocompatibility with the target cells and maintains cellular architecture intact while allowing cells to grow and live within its environment. The electrodes 124 and/or sensors 125 are positioned on the support and the collagen matrix introduced so that the cells grow on and around the electrodes 124 and/or sensors 125. The support preferably has a lattice or crossing pattern to enhance the growth of cells on the support.

The cell layers 132, 134 use the cellular characteristics of target cells to provide the sensing information. These cells provide sensing and individual cellular responses that can be measured by the sensors 125, such as pressure and deformation changes in cellular structure, photo-optical changes elicited by the cell. The ability to sense electrical (cardiac or neuronal electrical), chemical signals (chemoreception), and tension/pressure (flow/pressure transduction) by the device provides a broad range of clinical application for which it can be used. Devices can be individually tailored to measure the chemical of interest.

Figure 3:
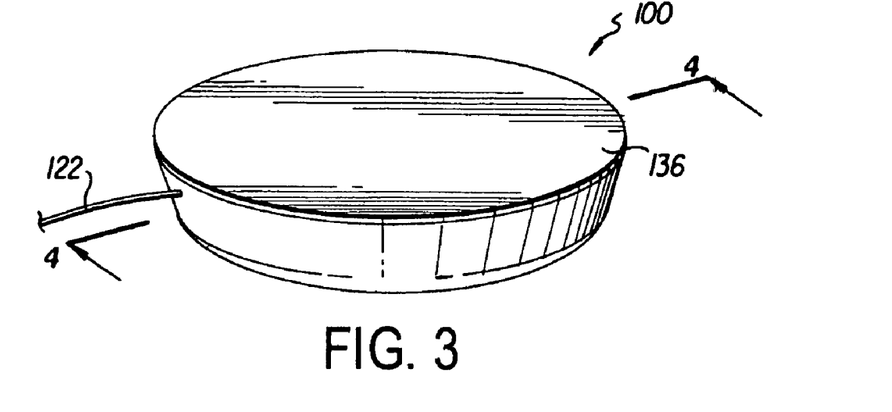
FIG. 3. is a perspective view of the bio-electro-physiologic device.
Figure 4:
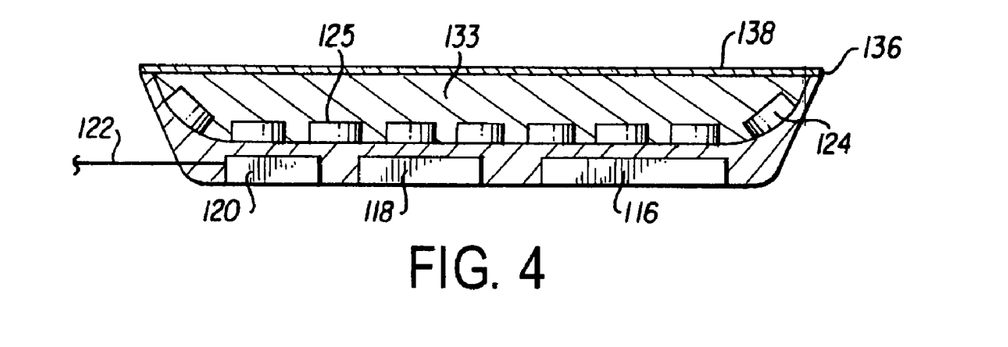
FIG. 4 is a cross section view of the bio-electro-physiologic device of FIG. 3.

FIGS. 3 and 4 show one embodiment of the invention, in which the device 100 has a tapered disc shape. As best shown in FIG. 4, a single cell matrix layer 133 is provided, with electrodes 124 and sensors 125 embedded at the bottom of the layer 133. The amplifier 116, processor 118, and communications device 120 are located below the cell layer 133, and are preferably hermetically sealed separate from the cell layer 133 so that they do not get wet. As further shown, the biologic interface portion 130 includes an optional semi-permeable membrane 136 that covers the cell layers 132, 134. The thin semi-permeable membrane 136 allows bi-directional low of nutrients and gas (such as oxygen) to exchange between the patient and the cell layers 132, 134 and allow nutrients to flow through and be exposed to the cell layers 132, 134. The membrane 136 can be, for instance, a silicone or other biocompatible material that has sufficient openings or spaces (such as a fine mesh) that permit the exchange of nutrients, gas and signals, yet contain the cell matrix 133.

In addition, an optional coating 138 is applied to the outer surface of cell layer 132, 134, or to the membrane 136 (if one is provided), or to any exposed electrodes 124 or sensors 125 at the surface of the cell layer 132, 134. The coating 138 inhibits the formation of scar tissue or fibrotic growth over the device 100. The preferred coating 138 is GORE-TEX®, which is manufactured by Guidant and is suitable for high voltage applications, but can also be steroids or a combination of steroids and GORE-TEX®. Steroids dilute over time and eventually disappears.

Also, growth stimulator substances can be used to facilitate the integration of the device 100 with the surrounding tissue of the patient. The growth stimulator is applied to the electrodes prior to the cells being introduced to the electrodes. The growth stimulator stimulates the growth of the cells to the electrodes.

Though the electronics 110 and biologic interface 130 are separate from one another, they can also overlap with one another. Thus, the device 100 can have any suitable shape and size. The device can be round, with the cell layers 132 forming the outer surfaces and the electronics portion 110 sandwiched there between. The device 100 can also be oval-shaped or tubular.

This device 100 does not require permanent long lead electrodes to be placed in the body tissue or vascular system. By combining cellular biologic sensors with microcircuitry, and eliminating the need for a lead, the device 100 is small and can be placed in areas that are not accessible by chronic lead placement techniques. In addition, the device can have a wire 122 that networks together multiple devices 100, though networking can also be wireless. The device can be placed transvenous as well as subcutaneous and/or within organs such as brain, gastrointestinal tract and central nervous system.

The sensing is done by the cellular system that is integrated with the device to provides a response that is detected by the circuitry depending on tissue characteristics. The ability to directly select the cell type to be used as sensors provides a small sensor since those cells can be used to sense or react to certain patient conditions without the need for additional sensors which can detect multiple substances within the body and have specific response features that can then be translated into useful information.

The cells are selected based on their ability to detect and respond to the physiologic signal of interest. For example, if a response to circulating chemical messengers such as catecholamines is required information, then skeletal muscle may be used. Accordingly, those cells eliminate the need for a separate sensor to detect the desired chemical messenger. In this setting, the muscle is biopsied from the arm or leg and placed into an environment that allows separation of the cells in an atraumatic fashion so as to minimize damage. The cells are then grow onto the device. The site of growth includes direct contact with an array of electrodes or Micro-electromechanical devices. The electrode array interface may be in a single plane or the electrodes distributed within a three-dimensional architecture so that the cells are in direct contact with a variety of electrodes. When the cell have matured and attached themselves to the electrode/sensor circuitry/MEMs, then the device is prepared for implantation within the same person from whom the cells were obtained. Alternatively the cells may be from another human or non-human source and produced in such as way to be compatible with the person in whom it is implanted. This minimizes scar formation and rejection.

The device may also be placed within a vessel in direct contact with blood, or within other tissue such as adipose (fat) tissue, muscle, or specific organs including the spine and nervous system. The device can monitor the integrated biologic tissue (biopsied and grown cells) and notice if there is a change in electrical activity of the cell, increased contraction or stretch activity, or metabolic activity as it responds to the physiologic signal of interest.

In this scenario, the cells respond to increase in catecholamines by increasing their frequency of firing as well as strength of contraction, which is measured by a shear stress recording sensor 125, pressure via pressure transducer 125 and the rate of change of the mechanical conformational changes. The change in shear stress/pressure and/or electrical activity (amplitude and frequency) can be detected. The electrical activity is also recorded if it is the desired signal or cellular response that is used as a marker. The device then transmits the detection to an external controller or may have its own controller 118 that either stores and/or acts on the information by emitting an electrical stimulus to inhibit or stimulate the target organ in which the device is implanted. The data may also be wirelessly communicated, for example using ultrasonic sound, to another networked implanted or external device that then performs the intervention that may consist of electrical stimulation, or trigger an infusion of a substance by an implanted or external pump.

The device 100 can also provide information for use by other medical devices, such as a cardiac ventricular assist device to alter its flows and parameters to maximize cardiac output. The device 100 can alternatively be used to modulate blood pressure and central nervous system reflexes such as the baroreceptor reflex system from peripheral nervous system points or directly form the brain itself. It can also be used to predict events such as ventricular fibrillation or onset of seizure activity within the brain by detecting neuro-transmitter changes that can only be detected by biologic tissue.

The device 100 is able to stimulate tissue with a predetermined sub-threshold pacing and determine the response of the cell layers 132, 134 to obtain data regarding the cells perception of the body's physiologic processes. For example, a cell may slightly increase electrical frequency of depolarization in response to an event, but the device 100 may increase the sensitivity of the detection by stimulating the cell layers 132, 134 and study the response of the cell layers 132, 134 to the stimuli as a way of interpreting the signal. The stimulation triggers a response from the cells depending on the application. That evoked response provides information about the conditions being sensed by the cells.

Figure 5:
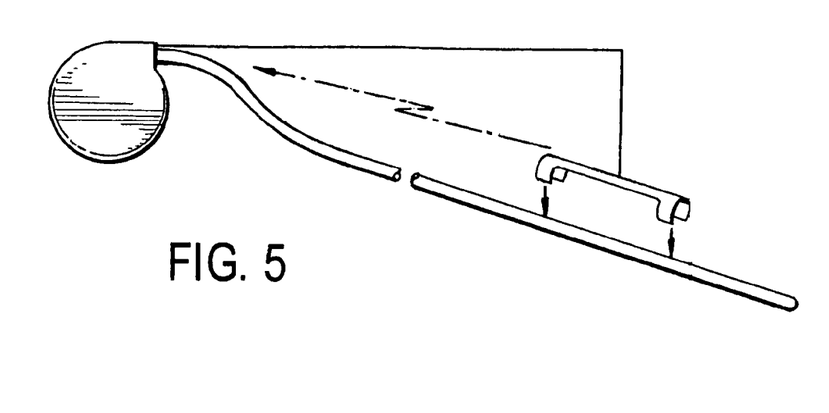
FIG. 5 is another embodiment of the device having a tubular stent-like shape attached to the lead of a pacemaker.

The device 100 can be placed anywhere in the body, including the abdomen and brain. However, the device 100 is preferably used as a wireless sensor and stimulator, but can also be used with existing devices such as pacemakers, ICD's, deep brain stimulator devices and pain control devices. For instance, as shown in FIG. 5, the device 100 can be formed in a tubular shape that is attached to the lead of a conventional pacemaker to operate as a sensor for the pacemaker, either as part of the lead or as an additional feature of the lead.

In a preferred embodiment of the invention, one or more devices 100 are implanted in a patient as remote sensors or electrodes that communicate with a controller to operate as a defibrillator, such as described in co-pending application serial number PCT/US2005/015379 entitled "Leadless Implantable Cardioverter Defibrillator" filed herewith, which claims priority to Ser. No. 60/567,449 filed May 4, 2004. The controller 118 can be used as a defibrillator to impart an electrical stimulation to the patient's heart. In addition, the device 100 can be configured for use as a stent or have a stent-like shape and be integrated with electronics as described in co-pending application serial number PCT/US2005/015374 entitled "Leadless Implantable Intravascular Electrophysiologic Device for Neurologic/Cardiovascular Sensing and Stimulation" filed herewith, which claims priority to Ser. No. 60/567,447 filed May 4, 2004. The contents of each of those applications is incorporated herein by reference.

Turning now to FIG. 6, shown therein is the embodiment of the invention previously described in the form of a complex collagen or other biocompatible support matrix 600 supporting a plurality of sensors 125 (as also seen in FIGS. 1 and 4). The matrix 600 can be formed into any suitable shape, including the 3-dimensional cubic structure shown in FIG. 6. The matrix 600 can be made as a scaffolding structure 602 using collagen or similar organic materials or from non-organic materials such as, for example, plastic, silicone, and metal. The scaffolding structure 602 may be, or be integrated with, wiring for electronic, optical, radio-frequency, ultrasonic, and other communications devices 120 (FIG. 2) between the sensor(s) 125 and the excitation emitter(s) 606, which may need to be conveyed through a biologic tissue/cellular material 612. The purpose of the matrix 600 is to provide a microenvironment within which the biologic tissue/cellular material 612 of a biological sample may be maintained. The cells of the biologic tissue/cellular material 612 themselves may provide a suitable scaffolding material.

The invention also contemplates the use of wireless communications between the sensor(s) 125 and the excitation emitter(s) 606. Ultrasonic sound may be used to convey information between the sensor(s) 125 and the excitation emitter(s) 606 and between and among different sensor(s) and emitter(s). The sensor(s) 125 may be built directly into or form an integral part of the scaffolding structure 602 or it may be supported within the interstitial spaces and cavities inside or outside the scaffolding structure 602.

The excitation emitter(s) 606 may be disposed interiorly or exteriorly of the scaffolding structure 602. As shown in FIG. 6, a single excitation emitter 606 is shown placed below and extending across a portion of the bottom of the scaffolding structure 602. The location of the excitation emitter(s) 606 may need to be determined based on the location of a biologic tissue/cellular material 612 in order to increase the efficacy of detecting radiation produced by or physical changes in the material 612 as a result of the excitation radiation 610 emitted from the excitation emitter(s) 606.

The fixed photonic sensors 125 are wavelength-specific detectors but may be intermingled with other sensors that have other properties. That allows multiple colors to be used and to sense/detect multiple intracellular signals at the same time. The individual sensors 125 can be controlled as a group or sub-group to allow specific detection of certain light signals while filtering or ignoring other signals, or they can operate simultaneously to allow concurrent analysis of the light signal obtained at various wavelengths. For example, a detection array may consist of five different detectors in various concentrations or proportions; they can be individually turned on/off and grouped according to functionality needed.

Moreover, the sensor(s) 125 and excitation emitter(s) 606 may be positioned at various depths within the scaffolding structure 602 to allow for phase contrast light detection at various depths within the matrix. That would provide access to various layers of the cell material 612 that may provide for better signal-to-noise ratio.

Figure 7:
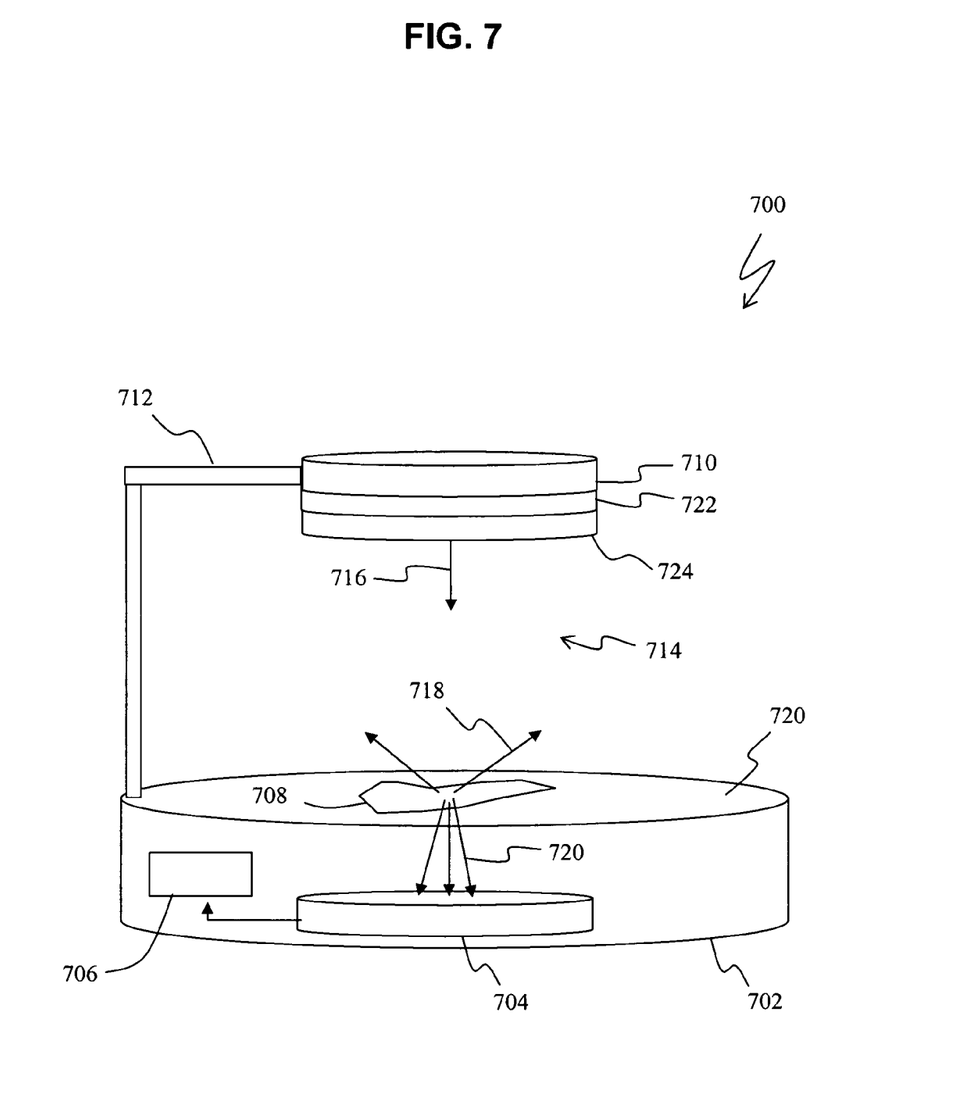
FIG. 7 is a drawing showing an arrangement of a sensor and excitation emitter according to another embodiment of the present invention.

Turning now to FIG. 7, shown therein is another arrangement of a sensor 702 and excitation emitter 710 in proximity to the sensor 702 according to an embodiment of the present invention. The sensor 702 includes a substrate or platform 720 for supporting a biologic tissue/cellular sample material 708 and for supporting, as needed, an integrated support member 712 that connects the sensor 702 to the excitation emitter 710.

The sensor 702 may also include a built-in power source, power controller, logic and communications circuits, analog-to-digital converter circuits, and a memory device as depicted by reference number 706. The location of those elements may be associated with the sensor 702 or remotely positioned external of the sensor 702. Those elements may also service more than one sensor 702. For example, a remote power source may be used to power the sensor 702 and the excitation emitter 710 shown in FIG. 7, and it may also be used to power a separate sensor and excitation emitter (not shown).

Also part of the sensor 702 is a photodetector 704, which is designed to detect radiation emitted by the sample 708. Photodetectors, like charged coupling devices (CCDs) common in the art, may be used as the photodetector 704. Any device capable of detecting wavelength-specific radiation 720 and ignoring scatter radiation 718 and that is adapted to output an electronic signal representative of the magnitude/intensity of the radiation 720, is suitable for that purpose.

It should be noted that the space separating the sensor 702 and the excitation emitter 710, designated by reference number 714, should be large enough to accommodate the mass transfer of nutrients into the area proximate the material 708, to allow gases and by-products from the material 708 to be removed from the area proximate the material 708, and should be appropriately sized to provide adequate heat transfer to ensure physiological mechanisms are sufficiently maintained, such as basic metabolism. The size of the space 714 will depend on the size of the material 708.

In addition to being a source of monochromatic, polarized, filtered, and wavelength-specific radiation, the excitation emitter 710 can also function as a shape/edge detector that is used to detect responsive movements in the biologic tissue sample 708 caused by the excitation radiation 716 that impacts the sample 708 (e.g., changes is size due to contraction of cells). That can be accomplished using an edge detection algorithm and light sensing ability to detect a change in shape of the biologic sample material 708, which is performed by measuring the outer circumference of the material 708 and comparing where light amplitude was blunted or blocked. For example, muscle tissue would contract to a response causing a micron-size shortening of the tissue. That change is size exposes more of the sensor 702 to be exposed to radiation. It would also cause an increase in tissue density near the center of the tissue material 708 that may be picked up by change in light absorbance or intensity correlating with the shape change or shortening of the circumferential edge of the tissue material 708.

Either the excitation emitter(s) 710 or the sensor(s) 702 may include an adjustable focal length either via a lens or lenses 722, which are step motor controlled, or via an optical filter or filters 724 that can be moved to adjust for depth or angles (shown in FIG. 7 as being relative to the excitation emitter(s) 710).

With regard to the biologic tissue/cellular material 612, 708, the cells may be layered and grown on the sensors 125, 702 themselves, or they may be grown proximate a light source. The devices shown in FIGS. 6 and 7 can also detect local fluid properties, such as pH and oxygen content, by taking advantage of substances that transiently change their fluorescence in response to changes in pH, oxygen, carbon dioxide.

Figure 8A:
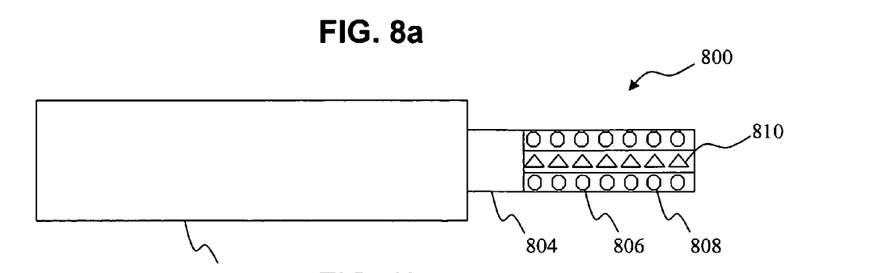
FIG. 8a is drawing showing a top plane view of a matrix showing an alternative method of arranging sensors and excitation emitters.
Figure 8B:
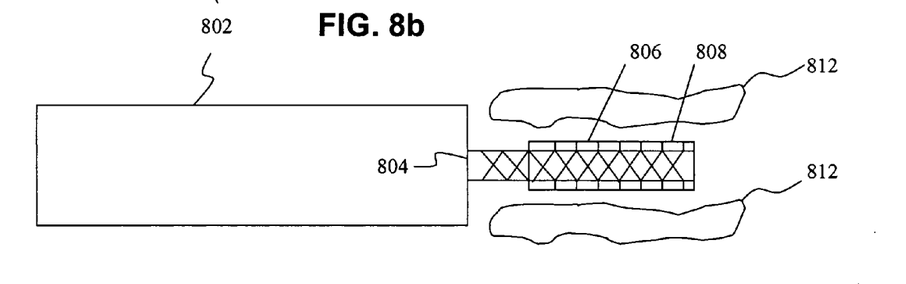
FIG. 8b is a drawing showing a side plane view of the matrix in FIG. 8a inserted in and partially supporting through direct contact a biologic tissue/cellular material sample.
Figure 8C:
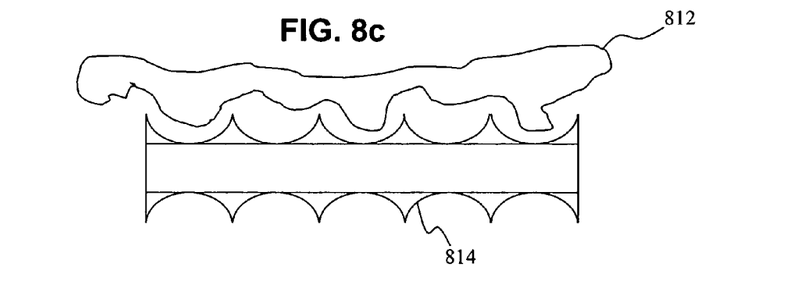
FIG. 8c is a drawing illustrating the use of concave sensors on the matrix.
Figure 8D:
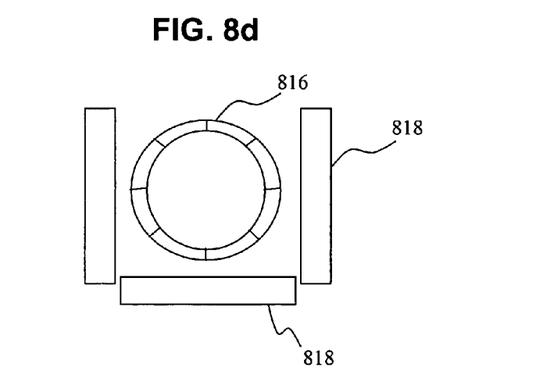
FIG. 8d is a drawing illustrating another configuration of the matrix.

Turning now to FIG. 8a, shown therein is top plan view of a matrix device 800 showing an alternative method of arranging the sensors 806, 808 and excitation emitters 810 on the tip of a matrix 804. The matrix 804 is connected to a circuit component 802 which may be directly attached to the matrix 804 or remote from the matrix 804 (i.e., connected by electrical leads). FIG. 8b shows a side plan view of the matrix device 800 with the matrix 804 inserted in and partially supported through direct contact a biologic tissue/cellular material sample 812, which is partially inside and outside of the matrix 804. FIG. 8c illustrates the use of concave sensors 814. FIG. 8d illustrates yet another configuration for the matrix in which a plurality of sensors 816 are arranged in a cylindrical fashion and are surrounded tangentially by an array of excitation emitters 818 on one, two, three, four, or more locations around the sensors 816.

Figure 9:
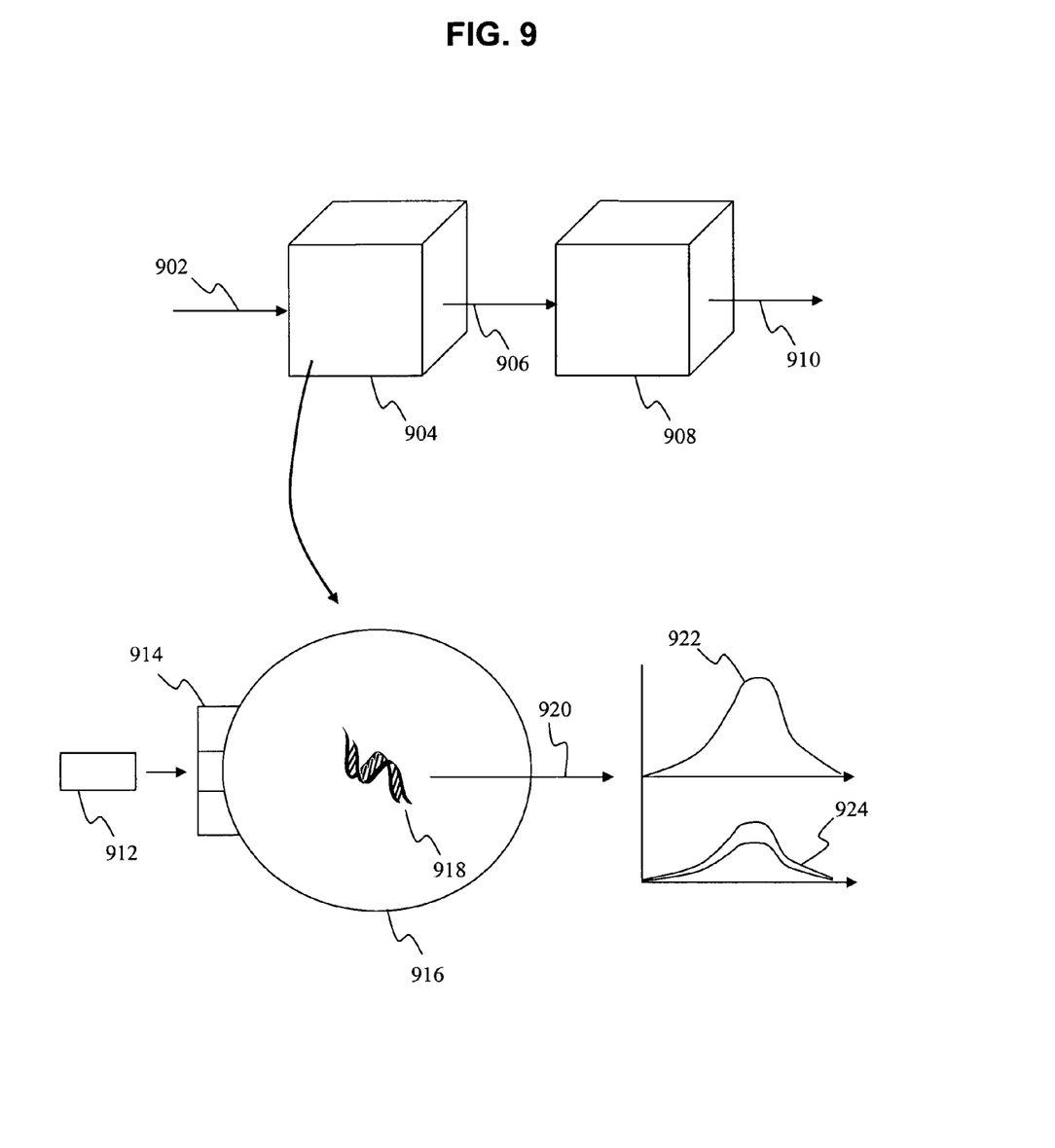
FIG. 9 is a drawing depicting a method of using the matrix.

An illustration of the method of using the matrix described above is shown in FIG. 9. In FIG. 9, an excitation signal 902 is emitted by an excitation emitter (not shown) in the form of radiation that enters a matrix 904, which, as described previously, includes a cell cluster. Within the cell cluster are cells such as cell 916 having surface receptors 914. The surface receptors 914 are integral to the membrane proteins of the cell 916.

When a biologic signal 912 interacts with the receptors 914, together they form a triggering mechanism that modulates the cell's 916 activity. As shown in FIG. 9, one triggering mechanism sets off a DNA response that causes a protein 918 to be synthesized by the cell 916. That protein 918 has certain physical properties, including the ability to fluoresce upon absorption of certain wavelengths of radiation 912. Alternatively, a detection protein, like green fluorescent protein (GFP) from jellyfish, may be attached to the protein 918 (other detection substances may also be used). GFP emits a bluish light 920 in the range of 508-515 nanometers (nm) wavelength when excited with radiation having a wavelength in the range of about 375-395 nm. Either way, the more protein 918 present in the cell, the higher the fluorescence intensity. Alternatively, an intracellular dye may also be used instead of GFP.

Thus, while the matrix 904 acts as a sensory device, it can be used to analyze the physiology of living biologic materials. The ability to use sophisticated micro-photonic technology sensors in addition to electrical, chemical, and pressure transduction, increases the potential types of signals that can be detected. The sensors of the present invention use wavelength-specific light to scan the cell or biologic material and provide information regarding its status and any changes that are relevant. Specific examples, in addition to those described above, include infrared scanning of cells to provide detection (i.e., via frequency of pulsations or change in contractility, or metabolism), which is a passive form of scanning and can be accomplished at various wavelengths to provide different information. Active photonic scanning, as described above, uses a light source and detection method within the same space for providing excitation and emission detection wavelengths. That can be done by using intrinsic cell material light absorption properties under certain conditions, or it can be done to enhance or take advantage of fluorescence or bioluminescence of the biologic material.

An excitation curve 922 is shown along with emission detection curves 924. The emission detection curves 924 are created from a photodetector output signal 906, which is then processed using appropriate analog-to-digital circuits and circuit logic algorithms as generally depicted by element 908. The output of the algorithm is a signal or information 910 that can be displayed on a computer graphical user interface or otherwise produced in a form for a user to interpret. For example, the output signal 910 may tell the user that the level of a material, the pH, or the amount of adrenaline is increasing or decreasing; it may also be used as a trigger for a different response.

It should be emphasized that the above-described embodiments of the present invention, and particularly, any preferred embodiments, are merely possible examples of implementations, merely set forth for a clear understanding of the principles of the invention. Many variations and modifications may be made to the above-described embodiments of the invention, without departing substantially from the spirit and principles of the invention. All such modifications and variations are intended to be included herein within the scope of this disclosure and the present invention and protected by the following claims.

I claim:

1. An implantable device for monitoring physiological changes in an organism, the device comprising:
   a matrix comprising a biocompatible support and cells of a biological material adhered within the matrix;
   an irradiation device associated with the matrix for exposing the cells of the biological material to radiation; and
   a sensor device associated with the matrix for detecting a response of the cells of the biological material to the irradiation, the response being reflective of a characteristic of the cells of the biological material.

2. The device of claim 1, wherein the matrix comprises a three-dimensional matrix.

3. The device of claim 1, wherein the matrix is made from a material comprising collagen.

4. The device of claim 1, wherein the biological material further comprises one of, a cell layer, nutrients, cellular reaction products, a physiologically acceptable dye, a physiologically acceptable marker, or a detection protein prepared exogenously relative to the biological material.

5. The device of claim 4, wherein the cell layer includes cells obtained from a biological organism.

6. The device of claim 1, wherein the sensor device comprises at least one photodetector attached to or positioned proximate the matrix.

7. The device of claim 1, wherein the irradiation device comprises at least one excitation emitter attached to or positioned proximate to the matrix for producing light having a known range of wavelengths.

8. The device of claim 7, further comprising an optical lens for focusing the light and a filter for filtering the light.

9. The device of claim 1, further comprising a device for allowing heat and mass transfer to exchange from the biological material inside the matrix.

10. The device of claim 1, further comprising an electronic component contacting the matrix, wherein the electronic component comprises a wireless communication device.

11. The device of claim 10, wherein the wireless communication device uses at least one of electronic, optical, radio-frequency, and ultrasonic signals adapted to being conveyed through biologic material.

12. The device of claim 11, wherein the electronic device comprises a communication device that can network the device and with other devices.

13. The device of claim 1, wherein the characteristic is at least one of a pH value, a level of metabolic activity, an intracellular pressure, a concentration of an intracellular substance, and a physical dimension of the biological material.

14. A method for monitoring physiological changes in an organism using an implantable device, the method comprising the steps of:
- providing a matrix comprising a biocompatible support and cells of a biological material adhered within the matrix;
- providing an irradiation device associated with the matrix for exposing the cells of the biological material to radiation;
- providing a sensor device associated with the matrix for detecting a response of the cells of the biological material to irradiation;
- irradiating the cells of the biological material; and
- detecting a response, wherein the response is reflective of a characteristic of the cells of the biological material.

15. The method of claim 14, further comprising the steps of:
- harvesting the biologic material from the organism; and
- growing the cells of the biological material in the matrix.

16. The method of claim 14, wherein the biological material comprises a cell layer.

17. The method of claim 14, wherein the sensor device comprises at least one photodetector attached to or positioned proximate to the matrix.

18. The method of claim 14, wherein the irradiation means comprises at least one excitation emitter attached to or positioned proximate to the matrix for producing light having a known range of wavelengths.

19. The method of claim 14, further comprising the step of providing nutrients to the biological material inside the matrix.

20. The method of claim 14, further comprising the step of outputting a signal representing a characteristic of the biological material, wherein the characteristic is at least one of a pH value, a level of metabolic activity, an intracellular pressure, a concentration of an intracellular substance, and a physical dimension of the biological material.

21. The method of claim 14, further comprising the step of communicating information about the response using a signal transmitting and receiving device, the device adapted to using at least one of electronic, optical, radio-frequency, and ultrasonic signals.

* * * * *